US00PP18275P2

(12) United States Plant Patent
Vandenberg

(10) Patent No.: US PP18,275 P2
(45) Date of Patent: Dec. 4, 2007

(54) ***CHRYSANTHEMUM* PLANT NAMED 'YOROCK'**

(50) Latin Name: *Chrysanthemum×morifolium*
Varietal Denomination: Yorock

(75) Inventor: Cornelis P. Vandenberg, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 11/489,197

(22) Filed: Jul. 19, 2006

(51) Int. Cl.
*A01H 5/00* (2006.01)

(52) U.S. Cl. ..... Plt./287
(58) Field of Classification Search ..... Plt./287
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Chrysanthemum* plant named 'Yorock', characterized by its upright plant habit; dark green-colored foliage; freely and uniformly flowering habit; decorative-type inflorescences that are about 7 cm in diameter; attractive greyed purple-colored ray florets; strong peduncles; and good postproduction longevity.

1 Drawing Sheet

Botanical designation: *Chrysanthemum×morifolium.*
Cultivar denomination: 'Yorock'.

BACKGROUND OF THE INVENTION

The present invention relates to a new and distinct cultivar of *Chrysanthemum* plant, botanically known as *Chrysanthemum×morifolium,* commercially grown as a cut flower and hereinafter referred to by the name 'Yorock'.

The new *Chrysanthemum* is a product of a planned breeding program conducted by the Inventor in Salinas, Calif. and Alva, Fla. The objective of the program is to create and develop new cut *Chrysanthemum* cultivars having inflorescences with desirable floret coloration and good inflorescence form and substance.

The new *Chrysanthemum* originated from a cross-pollination made by the Inventor in March, 1999, in Salinas, Calif. of a proprietary *Chrysanthemum×morifolium* seedling selection identified as code number R834, not patented, as the female, or seed, parent with a proprietary *Chrysanthemum×morifolium* seedling selection identified as code number 1092, not patented, as the male, or pollen, parent. The new *Chrysanthemum* was discovered and selected by the Inventor as a single flowering plant within the progeny of the stated cross-pollination in a controlled environment in Alva, Fla. in March, 2000. The selection of this plant was based on its desirable ray floret color and good inflorescence form and substance.

Asexual reproduction of the new *Chrysanthemum* by terminal cuttings in a controlled environment in Alva, Fla. since May, 2000, has shown that the unique features of this new *Chrysanthemum* are stable and reproduced true to type in successive generations.

SUMMARY OF THE INVENTION

Plants of the cultivar Yorock have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yorock'. These characteristics in combination distinguish 'Yorock' as a new and distinct cultivar of *Chrysanthemum:*

1. Upright cut *Chrysanthemum* that is usually grown as a naturally spray.
2. Dark green-colored foliage.
3. Freely and uniformly flowering habit.
4. Decorative-type inflorescences that are about 7 cm in diameter.
5. Attractive greyed purple-colored ray florets.
6. Response time about 59 days.
7. Strong peduncles.
8. Good postproduction longevity with inflorescences and foliage maintaining good substance and color for about two weeks in an interior environment.

Plants of the new *Chrysanthemum* differ from plants of the female parent selection in the following characteristics:

1. Plants of the new *Chrysanthemum* are shorter than plants of the female parent selection.
2. Plants of the new *Chrysanthemum* flower more freely and earlier than plants of the female parent selection.
3. Plants of the new *Chrysanthemum* and the female parent selections differ in ray floret color as plants of the female parent selection have vibrant orange-colored ray florets.

Plants of the new *Chrysanthemum* differ from plants of the male parent selection in the following characteristics:

1. Plants of the new *Chrysanthemum* are shorter than plants of the male parent selection.
2. Plants of the new *Chrysanthemum* flower more freely and earlier than plants of the male parent selection.
3. Plants of the new *Chrysanthemum* and the male parent selection differ in ray floret color as plants of the male parent selection have light pink-colored ray florets.

Plants of the new *Chrysanthemum* can be compared to plants of the *Chrysanthemum* cultivar Falma, disclosed in U.S. Plant Pat. No. 5,996. In side-by-side comparisons conducted in Alva, Fla., plants of the new *Chrysanthemum* differed from plants of the cultivar Falma in the following characteristics:

1. Plants of the new *Chrysanthemum* had shorter peduncles than plants of the cultivar Falma.
2. Plants of the new *Chrysanthemum* flowered about one week earlier than plants of the cultivar Falma.
3. Plants of the new *Chrysanthemum* flowered more freely than plants of the cultivar Falma.
4. Plants of the new *Chrysanthemum* had slightly larger inflorescences than plants of the cultivar Falma.
5. Plants of the new *Chrysanthemum* and the cultivar Falma differed in ray floret coloration.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the top of the sheet comprises a side perspective view of a typical flowering stem of 'Yorock' grown as a disspray type.

The photograph at the bottom of the sheet comprises a close-up view of typical inflorescences of 'Yorock' grown as a disspray type.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Bogota, Colombia in a polyethylene-covered greenhouse and under conditions and practices which approximate those generally used in commercial *Chrysanthemum* production. During the production of the cut flowers, day temperatures ranged from 20° C. to 25° C., night temperatures ranged from 4° C. to 9° C. and light levels ranged from 3,000 to 4,000 foot-candles. Measurements and numerical values represent averages for typical flowering plants. Plants were grown as disspray cut *Chrysanthemums*. The photographs and measurements were taken when plants were about three months old.

Botanical classification: *Chrysanthemum×morifolium* cultivar Yorock.

Parentage:

*Female, or seed, parent.*—Proprietary seedling selection of *Chrysanthemum×morifolium* identified as code number R834, not patented.

*Male, or pollen, parent.*—Proprietary seedling selection of *Chrysanthemum×morifolium* identified as code number 1092, not patented.

Propagation:

*Type.*—Terminal vegetative cuttings.

*Time to initiate roots.*—About ten to 14 days with soil temperatures of about 18° C. to 21° C.

*Root description.*—Fine, fibrous; white in color.

*Rooting habit.*—Freely branching.

Plant description:

*Appearance.*—Herbaceous decorative-type cut flower that is typically grown as a disspray type.

*Flowering stem description.*—Aspect: Erect. Length: About 101 cm. Diameter: About 7 mm. Internode length: about 3 cm. Texture: Pubescent; longitudinally ridged. Color: 146A.

*Foliage description.*—Arrangement: Alternate; simple. Length: About 8.5 cm. Width: About 3.7 cm. Apex: Acuminate. Base: Attenuate with truncate tendencies. Margin: Palmately lobed; sinuses mostly parallel. Texture, upper and lower surfaces: Pubescent; veins prominent on lower surface. Color: Developing foliage, upper and lower surfaces: 147A. Fully expanded foliage, upper surface: 147A; venation, 147B. Fully expanded foliage, lower surface: 147B; venation, 147B. Petiole: Length: About 1.5 cm. Diameter: About 3 mm. Texture, upper and lower surfaces: Pubescent. Color, upper and lower surfaces: 147B.

Inflorescence description:

*Appearance.*—Decorative-type inflorescence form with elongated oblong-shaped ray florets. Inflorescences borne on terminals, arising from leaf axils. Ray and disc florets develop acropetally on a capitulum. Uniformly flowering.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 59 days later when grown as a disspray type.

*Postproduction longevity.*—In an interior environment, inflorescences and foliage will maintain good color and substance for about two weeks in an interior environment.

*Quantity of inflorescences.*—Freely flowering habit, about eight to eleven inflorescences per stem develop.

*Spray width.*—About 16 cm.

*Inflorescence size.*—Diameter: About 7 cm. Depth (height): About 2.6 cm. Disc diameter: No disc florets observed. Receptacle diameter: About 2.2 cm. Receptacle height: About 1.1 cm.

*Inflorescence buds.*—Shape: Ovoid. Height: About 1.8 cm. Diameter: About 1.2 cm. Color: 183A.

*Ray florets.*—Shape: Elongated oblong to ligulate. Surface: Concave to flat. Aspect: About 45° to 60° from vertical. Length, outer ray florets: About 4 cm. Width, outer ray florets: About 9 mm. Apex: Acute. Base: Attenuate. Texture: Smooth, glabrous; velvety; longitudinally ridged. Number of ray florets per inflorescence: About 252 arranged in numerous rows. Color: When opening, upper surface: 185A. When opening, lower surface: 178B. Fully opened, upper surface: Rustier than 185A; color does not fade with development. Fully opened, lower surface: 180B.

*Disc florets.*—No disc florets observed.

*Phyllaries.*—Quantity per inflorescence/arrangement: About 28 arranged in about three to four whorls. Length: About 8 mm. Width: About 3 mm. Shape: Elliptical. Apex: Acute. Base: Truncate. Margin:

Entire. Texture, upper surface: Smooth, waxy. Texture, lower surface: Pubescent. Color, upper surface: 147B. Color, lower surface: 148A.

*Peduncles.*—Length: First peduncle: About 12 cm. Fourth peduncle: About 18.5 cm. Seventh peduncle: About 21 cm. Diameter: About 3 mm. Angle: About 30° from vertical. Strength: Strong. Texture: Pubescent; longitudinally ridged. Color: 148B.

*Reproductive organs.*—Androecium: None observed. Gynoecium: Pistil length: About 6 mm. Stigma shape: Bi-parted. Stigma color: Close to 4A. Style length: About 3 mm. Style color: Close to 4C. Ovary color: Close to 145C.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* have demonstrated good tolerance to low temperatures of about 4° C. and high temperatures of about 35° C.

It is claimed:

1. A new and distinct *Chrysanthemum* plant named 'Yorock' as illustrated and described.

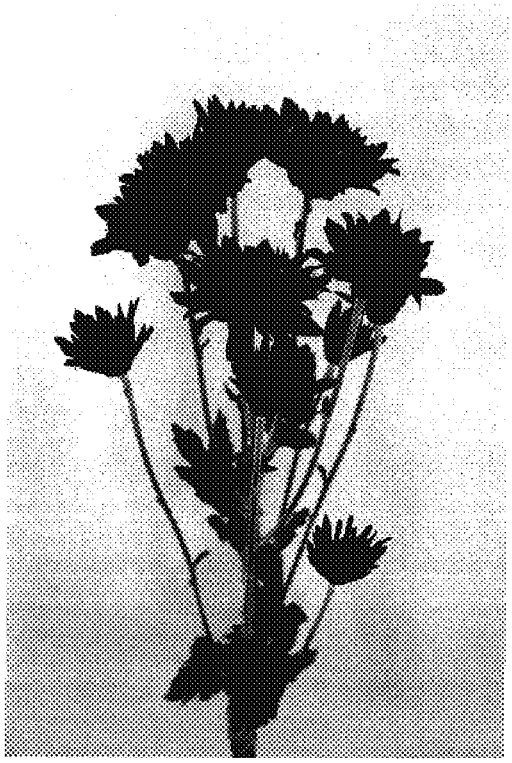
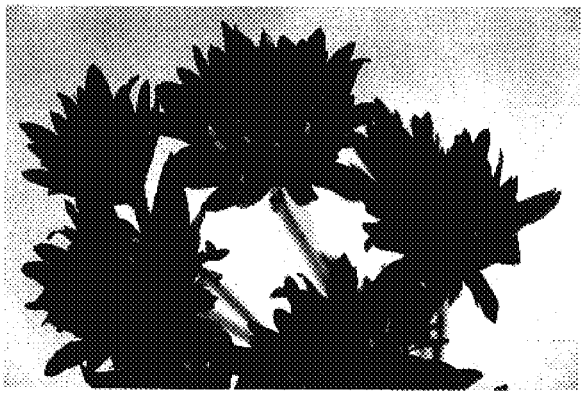

* * * * *